(12) United States Patent
Smith et al.

(10) Patent No.: US 7,976,796 B1
(45) Date of Patent: Jul. 12, 2011

(54) CENTRIFUGE TUBE FOR SEPARATING AND ASPIRATING BIOLOGICAL COMPONENTS

(75) Inventors: Emery Smith, Fort Myers, FL (US);
Patrick Pennie, Fort Myers, FL (US);
David K. Buzenius, Fort Myers, FL (US)

(73) Assignee: Emcyte Corp., Fort Myers, FL (US)

( * ) Notice: Subject to any disclaimer, the term of this patent is extended or adjusted under 35 U.S.C. 154(b) by 0 days.

(21) Appl. No.: 12/459,218

(22) Filed: Jun. 29, 2009

Related U.S. Application Data

(60) Provisional application No. 61/133,893, filed on Jul. 3, 2008.

(51) Int. Cl.
*B04B 7/00* (2006.01)

(52) U.S. Cl. .......... 422/548; 422/549; 422/550; 494/43; 494/45; 494/67; 222/249; 222/464.6

(58) Field of Classification Search .................. 494/43, 494/45, 67; 422/548, 549, 550; 222/249, 222/464.6
See application file for complete search history.

(56) References Cited

U.S. PATENT DOCUMENTS

| | | | | |
|---|---|---|---|---|
| 4,142,668 A * | 3/1979 | Lee | ................................. | 494/36 |
| 4,152,270 A * | 5/1979 | Cornell | ......................... | 210/516 |
| 4,154,690 A * | 5/1979 | Ballies | .......................... | 210/516 |
| 4,443,345 A * | 4/1984 | Wells | ............................. | 210/782 |
| 6,733,433 B1 * | 5/2004 | Fell | .................................. | 494/37 |
| 2004/0256331 A1 * | 12/2004 | Arking et al. | ................. | 210/787 |
| 2005/0124073 A1 * | 6/2005 | Freund | .......................... | 436/177 |
| 2005/0274679 A1 * | 12/2005 | Kao et al. | ...................... | 210/787 |
| 2006/0196885 A1 * | 9/2006 | Leach et al. | .................... | 222/82 |

FOREIGN PATENT DOCUMENTS

WO  WO 2005039773 A1 *  5/2005

* cited by examiner

*Primary Examiner* — Yelena G Gakh
*Assistant Examiner* — Christopher A Hixson
(74) *Attorney, Agent, or Firm* — William E. Noonan

(57) ABSTRACT

A centrifuge tube assembly includes an elongate tubular receptacle having a capped upper end. The capped upper end includes a single inlet/outlet port formed therethrough for communication with an interior of the tubular receptacle. A flexible aspiration pipe is communicably engaged with the inlet/outlet port for extending longitudinally through the cylindrical receptacle. A sealing diaphragm is attached to a distal end of the pipe. The diaphragm is longitudinally movable within the tubular receptacle and sealably interengages an interior wall of the receptacle. Biological products are introduced into and aspirated from the receptacle below the diaphragm by the fluid conducting pipe.

10 Claims, 2 Drawing Sheets

CENTRIFUGE TUBE FOR SEPARATING AND ASPIRATING BIOLOGICAL COMPONENTS

RELATED APPLICATION

This application claims the benefit of U.S. Provisional Patent Application Ser. No. 61/133,893 filed Jul. 3, 2008.

FIELD OF THE INVENTION

This invention relates to a centrifuge tube, which enables biological products such as blood, stem cells, bone marrow aspirate and the like to be separated into constituent components, and aspirated after the biological product has been centrifuged. The apparatus is particularly effective for sequestering platelet-rich plasma for use in surgical, medical and veterinary procedures.

BACKGROUND OF THE INVENTION

Platelet-rich blood plasma is required for use in various medical procedures. This blood product is particularly effective due to its growth promoting features, which assist greatly in wound healing and bone regeneration. Presently, blood plasma with a high concentration of platelets is utilized for dental implants and other periodontal procedures, facial reconstruction, oral or maxillofacial surgery and chronic wound care. In order to obtain a required concentration of platelets, a blood sample normally must be centrifuged in order to separate the blood into its component blood products (i.e. plasma, red blood cells and platelets). The platelets, typically in a form of a white "buffy coat", are then separated from the blood sample and sequestered in concentrated form through aspiration. Conventional aspiration techniques often fail to provide a satisfactory concentration of platelets. Cross-contamination between the constituent products is frequently encountered. We have determined that the need exists for a cost effective apparatus that facilitates the sequestration of platelets while minimizing cross-contamination between blood components.

To address the foregoing concerns, we developed the centrifuge tube assembly disclosed in U.S. Pat. No. 6,835,353. That apparatus incorporates one or more aspiration pipes into the centrifuge tube. Although that apparatus constitutes a significant improvement over the prior art and achieves superior results, we have determined that the need exists for an even simpler and more reliable design.

U.S. Pat. No. 7,179,391 features a centrifuge tube having a pair of buoys with differing densities mounted within the tube. The buoys float between and are intended to separate adjoining layers of constituent blood components after a blood product has been centrifuged and separated into those components. As a result, platelets are held in an intermediate layer in the tube between the buoys. An aspiration tube formed for the upper buoy allows the platelets to be aspirated from the tube. This apparatus is fairly intricate and thus quite expensive and complicated to manufacture. A substantial need exists for a far simpler and more efficient centrifuge tube for separating and aspirating blood components.

Indeed, an improved centrifuge tube is needed for separating and aspirating a host of biological products, including but not limited to blood products, bodily fluids, stem cells, bone marrow aspirate, etc. for use in both medical and veterinary applications. It is important for such products to be separated into constituent components quickly, effectively and without causing cross-contamination of those components.

SUMMARY OF THE INVENTION

It is therefore an object of the present invention to provide a simpler, more efficient and yet highly reliable centrifuge tube that enables blood and other biological products to be separated into constituent components and aspirated following separation.

It is a further object of this invention to provide a centrifuge tube with aspirating capabilities that is manufactured much less intricately and far less expensively than existing devices of this type.

It is a further object of this invention to provide an aspirating centrifuge tube that is much simpler to operate than devices of the type disclosed by U.S. Pat. No. 7,179,391.

It is a further object of this invention to provide a centrifuge tube that permits a host of chemicals, bodily fluids and other biological products to be separated and individually aspirated with minimal cross-contamination.

It is a further object of this invention to provide a centrifuge tube that is particularly effective for sequestering a high concentration of platelet-rich plasma for use in various medical, surgical and veterinary procedures.

It is a further object of this invention to provide an aspirating centrifuge tube that may be used effectively for separating and aspirating a wide range of biological products, including but limited to blood, stem cells, bone marrow aspirate, etc.

It is a further object of this invention to provide a centrifuge tube that may be used effectively in various medical and veterinary applications.

This invention features a centrifuge tube assembly having an elongate tubular receptacle and a capped upper end. A single common inlet and outlet port is formed in the capped upper end for communicating with an interior of the tubular receptacle. A single, flexible fluid conducting pipe is communicably connected to the common inlet/outlet port for extending through the tubular receptacle. A sealing diaphragm is mounted within the tubular receptacle for sealably engaging the interior wall of the tubular receptacle and moving longitudinally through the receptacle. The fluid conducting pipe is disposed through the diaphragm such that a distal end of the pipe communicates with the receptacle below the sealing diaphragm. Blood product or other biological fluid is introduced through the inlet/outlet port and fluid conducting pipe into the tubular receptacle below the sealing diaphragm. The sealing diaphragm is driven upwardly within the tubular receptacle as the fluid is introduced. The tube assembly is then centrifuged to separate the fluid into constituent components. One or more layers of separated fluid may then be aspirated through the fluid conducting pipe and the communicably interengaged inlet/outlet port.

In a preferred embodiment, the capped upper end is permanently sealed to the tubular receptacle. An opposite lower end of the tubular receptacle may include a flat base for supporting the tubular receptacle to extend upwardly from an underlying surface. A vent hole may be formed through the capped upper end and into the tubular receptacle for neutralizing pressure within the receptacle.

The diaphragm may include a sealing disk that is slidable longitudinally within the tubular receptacle while maintaining peripheral sealing engagement with the interior wall of the tubular receptacle. The fluid conducting pipe may be formed centrally through the sealing disk.

A method of separating biological product into constituent components using the foregoing assembly is also featured. Initially, a blood sample or other biological product is introduced into the tubular receptacle through the common inlet/outlet port and the attached fluid conducting pipe. As biological product is introduced into the tubular receptacle, it pushes the sealing diaphragm upwardly within the tubular receptacle. When the receptacle is filled to a desired level, the inlet/outlet port is covered and the assembly is centrifuged to separate the product into constituent components. The cover is then removed from the inlet/outlet port and one or more of the constituent components are aspirated through the fluid conducting pipe and communicably attached inlet/outlet port. As successive layers of constituent components are removed from the centrifuge tube, the sealing diaphragm descends through the tubular receptacle and the attached fluid conducting pipe is straightened or extended.

DETAILED DESCRIPTION OF PREFERRED EMBODIMENTS

Other objects, features and advantages will occur from the following description of a preferred embodiment and the accompanying drawings, in which.

Figure 1:
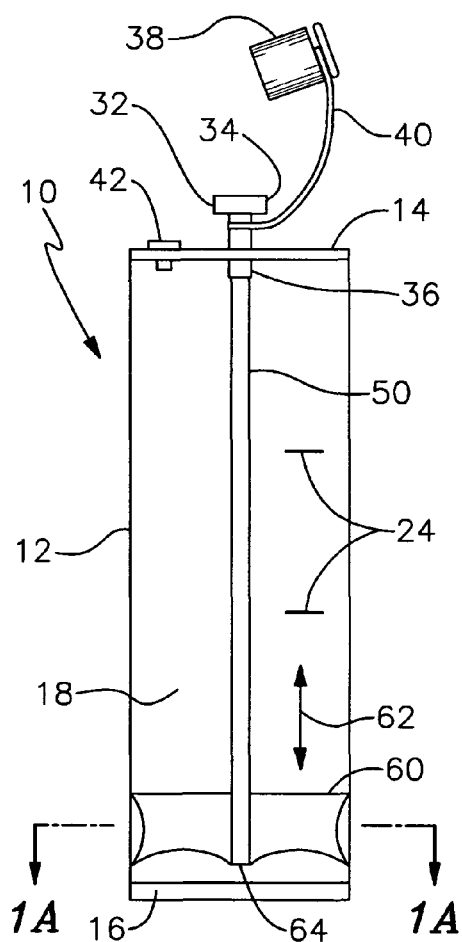
FIG. 1 is an elevational cross sectional view of the centrifuge tube assembly of this invention without any fluid or other biological product within the tubular receptacle.

There is shown in FIG. 1 a centrifuge tube assembly 10 that includes a tubular or cylindrical receptacle 12 having a permanently capped or closed upper end 14. A flat base 16 is similarly formed at the lower end of tubular receptacle 12 for supporting the tubular receptacle in an upright condition on a table or other flat or horizontal surface. In this way, the centrifuge tube assembly does not require a separate rack or holder for support.

As used herein, "centrifuge tube" should be understood to comprise various shapes and sizes of vessels, receptacles and containers having an interior chamber for holding a fluid biological product and capable of being centrifuged to separate the product into constituent components. The centrifuge tube is not limited to just tubular and elongate configurations, although such configurations will typically be used in preferred embodiments of the invention.

Tubular receptacle 12, as well as capped upper end 14 and base 16, are typically composed of a durable plastic material such as polypropylene or other material suitable for medical or veterinary applications. The tube should likewise be constructed to withstand the force exerted by centrifuging. In certain applications, shatter resistant glass may be employed. Although the tube is preferably formed with a permanently capped upper end, in alternative embodiments, a removable cap may be utilized. Various alternative and/or analogous forms of construction are disclosed in U.S. Pat. No. 6,835,353, the disclosure of which is incorporated herein by reference.

Tubular receptacle 12 includes an interior chamber 18 that extends from capped upper end 14 to base 16. This chamber accommodates blood, chemicals, stem cells, bone marrow aspirate or other biological fluids/products to be centrifuged and aspirated using assembly 10.

A plurality of graduated volume markings 24 may be formed at various selected intervals along the exterior side wall of tubular receptacle 12. Such markings should be formed at heights or intervals corresponding to commonly selected volumes of biological product that will be introduced into the tube. Such markings may be varied within the scope of this invention.

A common inlet/outlet port 32 is formed unitarily with capped upper end 14 of tubular receptacle 12. Port 32 includes a central opening that extends through capped upper end 14. The upper end 34 of port 32 is disposed exteriorly of the tubular receptacle whereas the lower end 36 of the port is disposed interiorly within chamber 18. Preferably, inlet/outlet port 32 is composed of polypropylene or other material similar to that forming the tube itself. Normally, the common inlet/outlet port is molded together with the tube in a single manufacturing process. Alternative types of inlet/outlet ports may be provided including Leur™ type ports as are described in U.S. Pat. No. 6,835,353. A removable closure 38 is secured to the outer stem 34 of port 32 by a connecting strap 40. During the centrifuging operation, as well as at other times when fluid is not being introduced into or removed from the tube, closure 38 is engaged with upper end 34 of port 32 to maintain the port in a closed condition.

A vent 42 is formed through capped upper end 14 adjacent inlet/outlet port 32. This vent maintains a stable neutral pressure within tubular receptacle 12 during the aspiration process. The vent may be formed at various locations in the capped upper end.

A single elongate, flexible pipe 50 is communicably engaged with inner end 36 of port 32. The pipe is composed of a flexible, yet strong, plastic material. Following initial manufacture of assembly 10 and prior to use of the assembly, pipe 50 maintains the elongate and relatively straight condition illustrated in FIG. 1. As is described more fully below, following addition of a biological product to the tube, pipe 50 is flexed or collapsed in the manner shown in FIG. 2. silicone or other flexible plastic material is especially suited for the pipe.

Figure 1A:
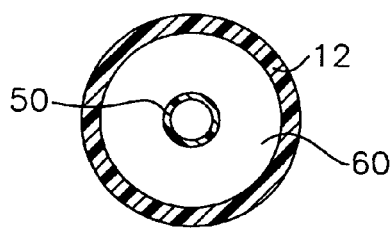
FIG. 1A is a cross sectional view taken along line 1A-1A of FIG. 1.
Figure 2:
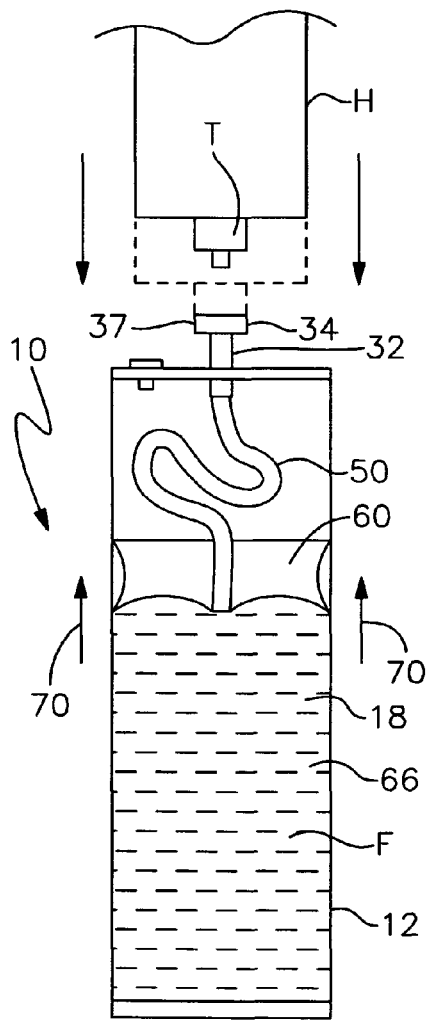
FIG. 2 is a view similar to FIG. 1 with a hypodermic needle positioned above the tube and with a biological fluid to be separated introduced into the tubular receptacle.

A disk shaped sealing diaphragm 60 is attached to the lower or distal end of pipe 50 and is itself slidably mounted for longitudinal movement within chamber 18 of tubular receptacle 12. More particularly, as also shown in FIG. 1A, diaphragm 60 has a circular, disk-like shape with a peripheral edge that sealingly and slidably interengages the interior wall of tubular receptacle 12. Diaphragm 60 is movable longitudinally within chamber 18 of tubular receptacle 12 as indicated by doubleheaded arrow 62, FIG. 1. As indicated in FIGS. 1 and 2, fluid conducting pipe 50 extends centrally through diaphragm 60 from the top surface to the bottom surface of the diaphragm. The lower or distal end 64 of pipe 50 communicates with an interior portion 66 of chamber 18 located below or beyond diaphragm 60.

As previously described, following manufacture of assembly 10 but prior to usage of that apparatus, sealing diaphragm 60 is positioned proximate the lower end or base 16 of receptacle 12. As a result, pipe 50 is fully extended in the manner shown in FIG. 1. Closure 38 is engaged with inlet/outlet port 32 so that the interior chamber 18 of receptacle 12 is sealed closed.

Figure 3:
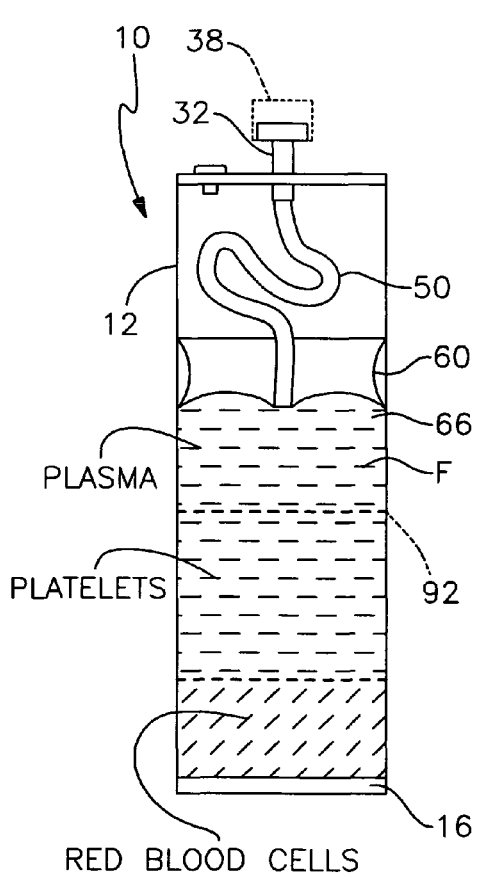
FIG. 3 is a view similar to FIGS. 1 and 2, wherein the tube assembly has been centrifuged to separate the fluid in the tube into three constituent components.
Figure 4:
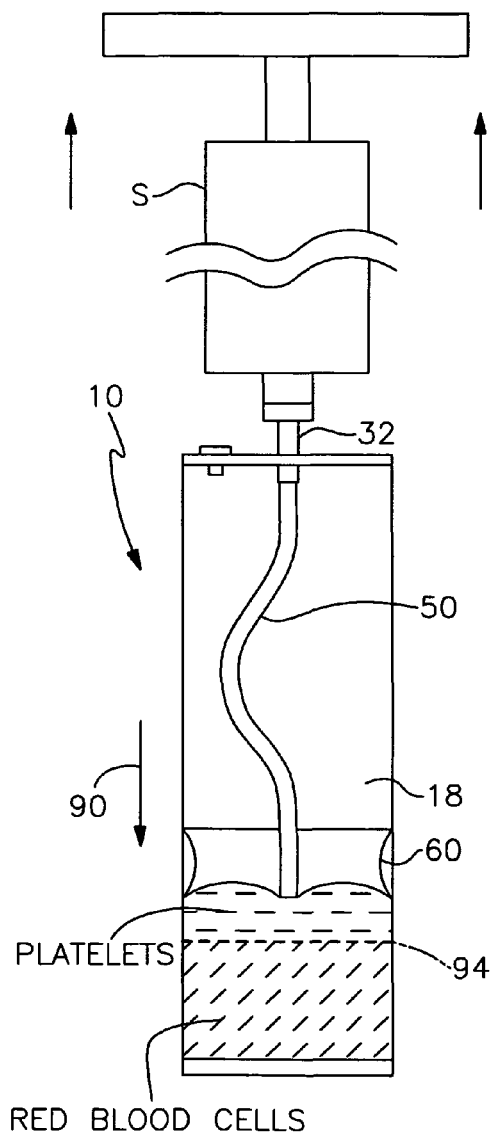
FIG. 4 is a view similar to FIGS. 1-3 wherein a hypodermic needled engaged with the tube is being operated to aspirate successive constituent components of the biological product from the tube.

Assembly 10 is utilized to centrifuge a biological product into its constituent components and then to aspirate one or more of those components as shown in FIGS. 2-4. A preferred use for centrifuge tube assembly 10 is the separation of a sample of blood into constituent blood components. Typically, it is desirable to separate the platelets from the red blood cells and plasma such that a platelet-rich blood product may be used in various surgical, medical or veterinary applications. This process is performed in the following manner. Initially, the empty receptacle 12 is stood on its base 16 as shown in FIG. 1 and closure 38 is removed from port 32. Blood product F (or an alternative biological product) is then added to receptacle 12 as depicted in FIG. 2. Specifically, a hypodermic syringe H carrying the blood or other biological product is operably engaged with upper end or stem 34 of inlet/outlet port 32. The tip T of hypodermic syringe H may be engaged with port 32 in a conventional manner. See U.S. Pat. No. 6,835,353. A lip 37 of upper portion 34 holds dispensing tip T securely in place so that the hypodermic syringe is securely engaged with assembly 10. The syringe is then operated in a conventional manner to introduce the product to be separated through port 32 and flexible pipe 50 into the interior chamber 18 of receptacle 12. More particularly, blood product or other biological product F is transmitted through pipe and sealing diaphragm 50 into the lower space 66 of chamber 18 located below or beyond diaphragm 60. As biological product F is introduced into space 66, the increasing volume of fluid product F pushes diaphragm 60 upwardly, as indicated by arrows 70. Blood product is added to the receptacle by syringe H in this manner until the level of fluid reaches a corresponding marking on the tube. As the diaphragm rises within chamber 18, in response to the rising volume of fluid F, the peripheral edges of diaphragm 60 remain in sealing engagement with the interior wall of receptacle 12. Flexible pipe 50 bends and collapses in the manner shown in FIG. 2. When a selected or desired amount of fluid has been added to the receptacle, hypodermic syringe H is disengaged from assembly 10. For human blood work, the selected volume of blood may be, for example, 50 ml. This volume is preferred because it typically yields approximately 5 ml of platelet-rich blood product. Other volumes may be used as required by a particular application.

After a desired amount of blood product or other biological product is introduced into the tubular receptacle, syringe H is disengaged from port 32 and closure 38 is reengaged with the port. Tubular receptacle 12 is then placed in a centrifuge, either by itself or with other tubular assemblies in accordance with this invention. The loaded centrifuge is operated in an established manner for a selected time (e.g. preferably 5-7 minutes) in order to separate the constituent components of blood or other fluid sample F. Various known types of centrifuge machines may be employed for this task. A single round or multiple rounds of centrifuging may be utilized so that the selected biological product F is separated into its constituent components.

After centrifuging is complete, assembly 10 is removed from the centrifuge and supported by its flat base 16 on a table or other support surface. In cases where fluid sample F comprises a blood sample, the centrifuged sample then appears as shown in FIG. 3. Specifically, centrifuging causes the red blood cells to collect in a dark layer at the bottom of receptacle 12. A discrete layer of plasma exhibiting a yellow color is formed at the upper end of chamber section 66 immediately beneath sealing diaphragm 60. An intermediate layer of platelets in the form of a white "buffy" coat is disposed between the plasma and red blood cells layers. In embodiments when other biological products are centrifuged, two or more discrete constituent component layers are formed in an analogous manner within the receptacle below the sealing diaphragm. In all cases, diaphragm 60 remains in sealing interengagement with the interior wall of receptacle 12 such that the biological component is maintained securely within the section 66 of chamber 18 below the diaphragm. Indeed, during the centrifuging process, the diameter of the disk-shape diaphragm typically expands somewhat to provide an even more securing sealing interengagement with the interior wall of the receptacle.

The user next aspirates one or more layers of the sequestered constituent components from the centrifuged fluid. This is accomplished by engaging one or more aspirating syringes S with assembly 10 in the manner shown in FIG. 4. For the blood product example that has been described herein, the user typically wishes to aspirate plasma and platelets using a pair of respective syringes S. Initially, the user removes closure 38, FIG. 3 and engages a first syringe with port 32. The syringe is operated to aspirate the upper layer of plasma from the chamber 18 through pipe 50 and port 32. Plasma is drawn through the pipe and common inlet/outlet port and into a respective syringe. As fluid F is removed from the tubular receptacle, air pressure urges sealing diaphragm downwardly as indicated by arrow 90 in FIG. 4.

Eventually, the diaphragm reaches the interface 92, FIG. 3, between the plasma and platelet levels. At this point, the user replaces the first syringe, which has been used to remove the plasma, with a second syringe designed to aspirate platelets. This is the particular syringe S depicted in FIG. 4. Aspiration continues using the syringe and platelets are removed through pipe 50 and port 32 into syringe S. Diaphragm 60 continues to descend within tubular chamber 18 while maintaining sealing interengagement with the interior wall of the tubular receptacle. As the diaphragm is driven downwardly through the tube, as indicated by arrow 90, the flexible pipe 50 is gradually re-extended in the manner shown in FIG. 4. Platelets are thereby aspirated into syringe 18 until the diaphragm reaches interface 94, which separates the platelets from the underlying red blood cell layer. When this interface is reached, aspiration is completed. The platelets and plasma can be utilized as needed for surgical/wound care procedures. The remaining red blood cells and sealed assembly 10 are disposed of in a medically acceptable manner. The permanently sealed nature of the container enables the used assembly and remaining red blood cells to be disposed of in a medically secure and relatively risk-free fashion.

Although the foregoing example depicts the use of centrifuge tube assembly in connection with the separation and aspiration of constituent blood components, it should be understood that the tube may be used equally effectively to separate and aspirate a wide variety of alternative biological products. These include stem cells, bone marrow aspirate and various other fluids/chemicals.

The centrifuge tube disposed here may be employed in a wide variety of medical, biomedical, veterinary and other types of procedures. When veterinary blood work is involved, the tube will typically comprise a much larger volume that is utilized during human blood work.

The devices and processes described above are particularly effective in allowing a blood sample to be conveniently separated into discrete blood products which may then be sequentially aspirated or removed so that a platelet-rich product is conveniently obtained. This entire procedure is performed without excessive mixing or cross-contamination of the individual components. The separation process is performed more quickly, inexpensively, efficiently and effectively then has hereto been possible using known centrifuge tubes. The present device is especially advantageous due to its use of relatively few working parts. Manufacturing of the assembly is thereby facilitated and its attendant cost is reduced considerably. By the same token, the centrifuge and aspiration process is performed much more quickly and easily then is accomplished using the apparatus of U.S. Pat. No. 7,179,391 for example.

It should be further understood that the centrifuge tube assemblies of this invention may be employed to separate various other types of biological products, fluids and chemicals. Likewise, in such applications the individual components may be sequestered and removed quickly and conveniently without undue mixing and cross-contamination.

In the foregoing description may be seen with the apparatus of this invention provides for an improved centrifuge tube which enables biological products to be effectively aspirated after they have been centrifuged.

From the foregoing it may be seen that the apparatus of this invention provides for a centrifuge tube, which enables biological products such as blood, stem cells, bone marrow aspirate and the like to be effectively separated into constituent components and aspirated after the biological product has been centrifuged. While this detailed description has set forth particularly preferred embodiments of the apparatus of this invention, numerous modifications and variations of the structure of this invention, all within the scope of the invention, will readily occur to those skilled in the art. Accordingly, it is understood that this description is illustrative only of the principles of the invention and is not limitative thereof.

Although specific features of the invention are shown in some of the drawings and not others, this is for convenience only, as each feature may be combined with any and all of the other features in accordance with this invention.

Other embodiments will occur to those skilled in the art and are within the following claims:

What is claimed is:

1. A centrifuge tube assembly for separating and aspirating constituent components of a fluid biological product, said assembly comprising:

an elongate receptacle having an interior chamber for receiving the fluid biological product therein, said receptacle having closed upper and lower ends and a side wall that extends between said upper and lower ends;

a common inlet and outlet port formed in said upper end of said receptacle for respectively introducing the fluid biological product into said receptacle and aspirating the constituent components of the fluid biological product from said receptacle;

a flexible, fluid conducting pipe communicably connected to said common port for extending through said chamber; and a liquid-impermeable sealing diaphragm mounted for sliding longitudinally through said chamber of said receptacle, said diaphragm maintaining sealing interengagement with an interior surface of said side wall of said receptacle during centrifugation of said receptacle, said flexible pipe being disposed through said diaphragm in communication with a region of said chamber located below said diaphragm; said common port for receiving the fluid biological product therethrough to introduce the fluid biological product through said pipe and into said chamber below said diaphragm and said receptacle being centrifuged to separate the fluid biological product into constituent components thereof, which components are disposed in respective fluid layers in said chamber, whereby one or more of the fluid layers may be aspirated through said pipe and said common port.

2. The assembly of claim 1 in which said upper end is integrally attached to said side wall of said receptacle.

3. The assembly of claim 1 in which said lower end includes a flat base for supporting said receptacle to extend upwardly from an underlying supportive surface.

4. The assembly of claim 1 further including a closure that is removably attached to said common port outside of said chamber for selectively opening said port to permit introduction of the fluid biological product into said chamber and aspiration of a separated constituent component therefrom and closing said port while said receptacle is being centrifuged.

5. The assembly of claim 1 further including a vent hole formed through said upper end and into said chamber for neutralizing pressure within said receptacle chamber as fluid is introduced into said chamber and as constituent components are aspirated from said chamber.

6. The assembly of claim 1 in which said diaphragm includes a sealing disk that is slidable longitudinally within said chamber while maintaining peripheral sealing engagement with the interior surface of said side wall of said receptacle.

7. The assembly of claim 6 in which said pipe is formed centrally through said sealing disk.

8. The assembly of claim 1 in which said diaphragm separates said chamber of said receptacle into upper and lower regions, said diaphragm restricting the passage of fluid between said upper and lower regions of said chamber to transmission of fluid through said flexible pipe and said upper region being devoid of fluid exteriorly of said pipe.

9. The assembly of claim 5 in which the air pressure within said chamber drives said diaphragm longitudinally through said chamber toward said lower end of said chamber as the constituent components are aspirated from said chamber.

10. The assembly of claim 1 in which the sealing engagement maintained between said diaphragm and said interior surface of said side wall of said receptacle during centrifugation of said receptacle prevents the passage of fluid between said diaphragm and said interior surface of said side wall during such centrifugation.

\* \* \* \* \*